United States Patent [19]

Maguire et al.

[11] Patent Number: 4,782,834

[45] Date of Patent: Nov. 8, 1988

[54] DUAL LUMEN DILATATION CATHETER AND METHOD OF MANUFACTURING THE SAME

[75] Inventors: Mark A. Maguire, San Jose; Lambert J. Diettrich, Danville; Nitin P. Matani, San Jose, all of Calif.

[73] Assignee: Advanced Cardiovascular Systems, Inc., Mountain View, Calif.

[21] Appl. No.: 647

[22] Filed: Jan. 6, 1987

[51] Int. Cl.[4] .............................. A61M 29/02
[52] U.S. Cl. ..................... 128/344; 604/96; 604/280
[58] Field of Search ............... 128/344; 604/93, 96, 604/103, 280; 156/304.6

[56] References Cited

U.S. PATENT DOCUMENTS

| | | | |
|---|---|---|---|
| 3,832,253 | 8/1974 | Palma et al. | 604/103 |
| 3,865,666 | 2/1975 | Shoney | 604/103 |
| 3,884,242 | 5/1975 | Bazell et al. | 604/103 |
| 3,985,601 | 10/1976 | Panagrossi | 604/103 |
| 4,385,635 | 5/1983 | Ruiz | 604/280 |
| 4,563,181 | 1/1986 | Wijayarathna et al. | 604/280 |
| 4,581,390 | 4/1986 | Flynn | 604/280 |

Primary Examiner—C. Fred Rosenbaum
Assistant Examiner—Gene B. Kartchner
Attorney, Agent, or Firm—Fulwider, Patton, Rieber, Lee & Utecht

[57] ABSTRACT

Dual lumen dilatation catheter and method of manufacture in which the catheter shaft is formed in a plurality of sections of different stiffness to provide optimum strength and flexibility at different points along the length of the catheter.

16 Claims, 1 Drawing Sheet

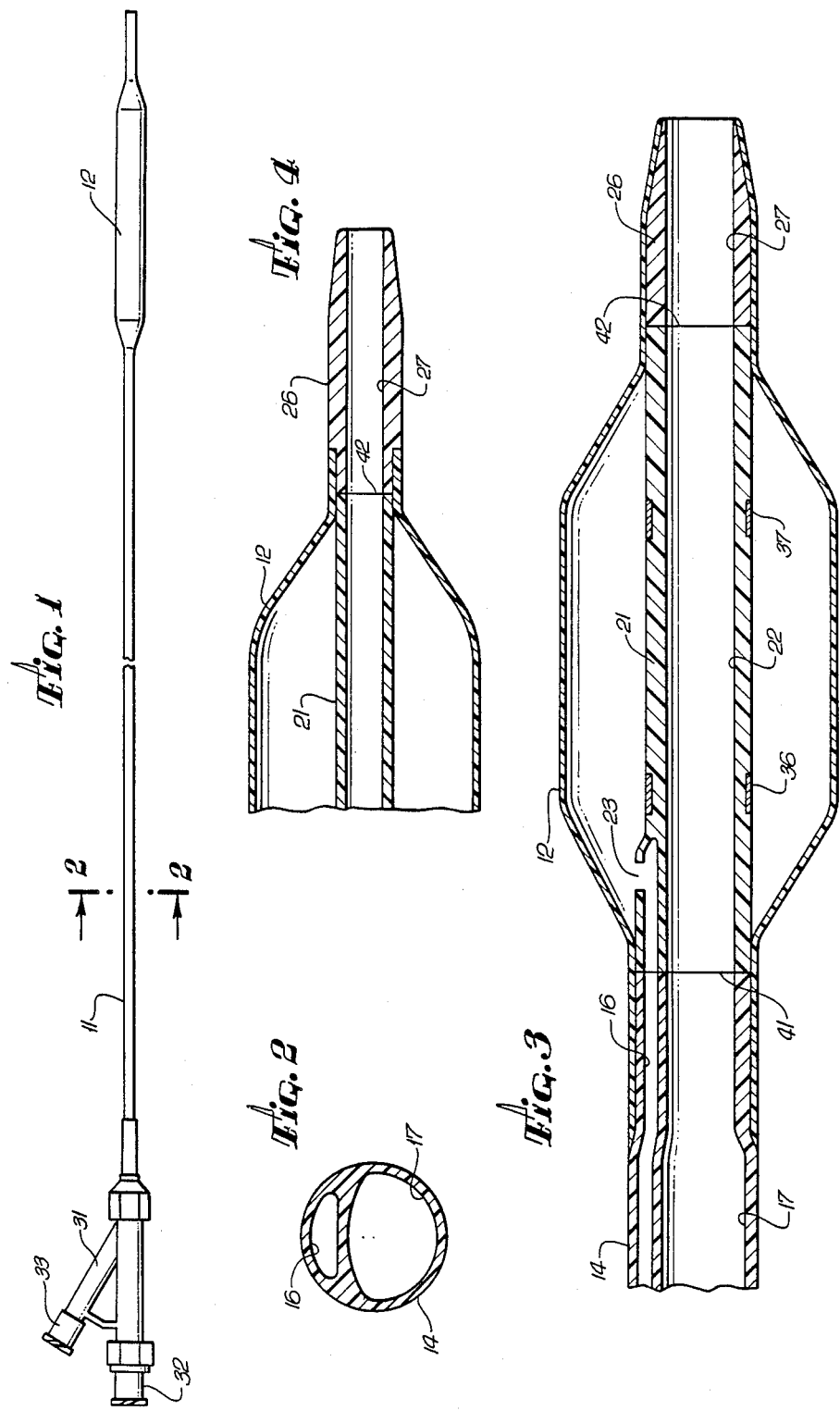

DUAL LUMEN DILATATION CATHETER AND METHOD OF MANUFACTURING THE SAME

This invention pertains generally to medical appliances, and more particularly to a dual lumen dilatation catheter for use in percutaneous transluminal angioplasty and to a method of manufacturing the same.

Dual lumen dilatation catheters heretofore provided generally have an elongated shaft with two longitudinally extending luminal openings positioned side by side therein, with an inflatable balloon sealed about the shaft near the distal end thereof in fluid communication with one of the luminal openings. The other luminal opening is utilized for a guide wire and for passing fluids to and from the vascular system. Such catheters are utilized primarily in peripheral (non-coronary) portions of the vascular system.

One problem with catheters of this type is that the walls of the shaft must be relatively thin in order to minimize the outer diameter of the shaft while making the luminal openings as large as possible. With these relatively thin walls, the portion of the shaft within the balloon tends to collapse when the balloon is inflated.

Another problem with the dual lumen catheters heretofore provided is that there is no variation in the strength or flexibility of the shafts along the length of the catheters, and this makes them difficult to position and steer within the vascular system.

It is in general an object of the invention to provide a new and improved dual lumen dilatation catheter and method of manufacturing the same.

Another object of the invention is to provide a catheter and method of the above character which overcome the foregoing and other limitations and disadvantages of dual lumen dilatation catheters heretofore provide.

These and other objects are achieved in accordance with the invention by providing a catheter in which the shaft is formed in sections of different stiffness joined together to provide optimum strength and flexibility over the length of the catheter. The first shaft section extends to the proximal end of the balloon and has a pair of longitudinally extending luminal openings. The second shaft section is polymerically stronger than the first section and is positioned within the balloon to provide adequate support and flexibility while resisting luminal collapse. This shaft section has a single luminal opening which communicates with one of the luminal openings in the first section. The other luminal opening in the first section is extended through the junction of the two sections during the formation of the junction and communicates with the interior of the balloon through an opening in the side wall of the second section. The third section extends from the distal end of the balloon to the distal end of the catheter and is fabricated of a relatively flexible material which gives the catheter a soft tip. The end portions of the balloon are sealed to the shaft over the junctions between the shaft sections to strengthen the junctions.

FIG. 1 is a side elevational view of one embodiment of a dual lumen dilatation catheter according to the invention.

FIG. 2 is an enlarged cross-sectional view taken along line 2—2 in FIG. 1.

FIG. 3 is an enlarged centerline sectional view of the distal end portion of the catheter of FIG. 1.

FIG. 4 is an enlarged centerline sectional view of the distal tip portion of another embodiment of a dilatation catheter according to the invention.

The catheter has an elongated shaft 11 with an inflatable balloon 12 near the distal end thereof. As described more fully hereinafter, the shaft is fabricated in three sections which are joined together to provide the desired shaft support, flexibility and diametral size at different points along the length of the catheter.

The first shaft section 14 extends between the proximal end of the catheter and the proximal end of the balloon and comprises a relatively flexible tubular member having a pair of longitudinally extending luminal openings 16, 17 positioned side by side therein. Opening 17 is somewhat larger than opening 16 and is adapted to receive a guide wire (not shown). Opening 16 is utilized for inflation and deflation of the balloon. In a typical catheter made in accordance with the invention, the shaft has an outer diameter on the order of 5 French (0.065 inch), opening 16 has a short diameter or height on the order of 0.012 inch, and opening 17 has a short diameter or height on the order of 0.039 inch. This catheter is suitable for use with a guide wire having a diameter on the order of 0.035 inch.

The second shaft section 21 extends from the distal end of section 14 to the distal end of the catheter. This section comprises a tubular member having a polymeric composition which provides a stronger yet more flexible shaft section than section 14 and has a single luminal opening 22 which communicates with the larger luminal opening 17 in the first shaft section. The smaller luminal opening 16 extends through the junction of the two shaft sections and communicates with the interior of the balloon through an opening 23 in the side wall of section 21.

The third shaft section 26 extends between the distal end of the balloon and the distal end of the catheter. This section comprises a flexible tubular member having a single luminal opening 27 which communicates with luminal openings 17 and 22 to form a continuous axial passageway for receiving a guide wire and carrying fluids to and from the vascular system.

Balloon 12 comprises a distensible tubular member which is positioned coaxially about flexible, collapse-resistant shaft section 21 and is sealed to the shaft at its proximal and distal ends to form a closed chamber which communicates with luminal opening 16 through opening 23 in the side wall of shaft section 21. The wall of the balloon is preferably made as thin as possible in order to minimize the overall diameter of the catheter where the balloon is sealed to the shaft. In a catheter having the shaft dimensions given above, the balloon typically has a diameter on the order of 4.0–7.0 mm when inflated.

A side arm adapter 31 is connected to the proximal end of the catheter. This adapter has a central port 32 which communicates with luminal opening 17 and a side port 33 which communicates with luminal opening 16. Bands 36, 37 of radiopaque material are mounted on shaft section 21 within the balloon to provide fluoroscopically visible markers by which the position of the balloon can be observed.

In one presently preferred embodiment, the three shaft sections and the balloon are fabricated of different blends of polyethylene selected to provide the desired degree of flexibility or strength for each portion of the catheter. In this embodiment, section 14 is relatively flexible, and section 21 is fabricated of a stronger blend which resists collapsing as the balloon is inflated. Section 26 is very flexible in order to provide a soft tip for the catheter.

The shaft sections are joined together by heat melting to form a unitary structure. The junction 41 between sections 14 and 21 is sealed beneath the proximal end portion of the balloon, and the junction 42 between sections 21 and 26 is sealed beneath the distal end of the balloon. The heat melted junctions permit a small shaft diameter under the balloon, enabling the balloon to have a low profile when it is collapsed. The heat melted junctions also permit precise control of flexibility characteristics in critical sections of the catheter without comprising the ability of the shaft to resist collapsing during balloon inflation or to maintain axial strength or "pushability". The heat seal between shaft sections 21 and 26 continues all the way to the distal end of the shaft, thereby providing a soft and flexible tip for the catheter to enhance its ability to follow or "track" smoothly along a guide wire.

With the polyethylene shaft sections, the proximal and distal end portions of the balloon are heat sealed to the shaft, and these heat seals extend beyond the heat melted junctions between the shaft sections. Since the end portions of the balloon overlie the junctions between the shaft sections, they tend to reinforce the junctions, giving the shaft added strength and support in these areas.

The embodiment illustrated in FIG. 4 is similar to the embodiments of FIGS. 1-3 except for the materials of which the shaft sections and the balloon are fabricated and the manner in which the balloon is sealed to the shaft. Like reference numerals designate corresponding elements in the two embodiments. In the embodiment of FIG. 4, the shaft sections and the balloon are fabricated of polyester tubing, and the catheter is designed primarily for high pressure balloon inflations. As in the previous embodiment, the tubing utilized in the different shaft sections is selected to provide the stiffness and flexibility desired at different points along the length of the catheter. The main shaft section is relatively flexible, the section within the balloon is relatively stiff, and the tip section is relatively flexible. The material of which the balloon is fabricated is relatively stiff, although it is thin enough to permit inflation of the balloon.

As in the embodiment of FIGS. 1-3, the shaft sections are joined together by heat melting, and the proximal end portion of the balloon is heat bonded to the shaft over the junction of shaft sections 14 and 21. The distal end portion of the balloon, however, extends only a short distance beyond junction 42 and is sealed to the shaft with an adhesive. This prevents the relatively stiff material of the balloon from detracting from the softness of the tip provided by the relatively soft, flexible material employed for shaft section 26. Also, in this embodiment, the outer surface of shaft section 26 is made flush with the outer surface of the distal end portion of the balloon 12.

It is apparent from the foregoing that a new and improved dual lumen dilatation catheter and method of manufacturing the same have been provided. While only certain presently preferred embodiments have been described in detail, as will be apparent to those familiar with the art, certain changes and modifications can be made without departing from the scope of the invention as defined by the following claims.

We claim:

1. A dilatation catheter for use in transluminal angioplasty having a longitudinally extending tubular member, said tubular member comprising:
   (a) a first tubular section formed of polymeric material having first and second longitudinally extending lumens positioned side by side with openings for each lumen at the distal end of said section;
   (b) a second tubular section formed of polymeric material having a longitudinally extending lumen joined to the distal end of the first tubular section with the first longitudinally extending lumen in the first tubular section in fluid communication with the longitudinally extending lumen in the second tubular section, the polymeric material of said second tubular section having a different flexibility from the polymeric material of the first tubular section to provide variable flexibility along the length of the tubular member of the catheter; and
   (c) an inflatable balloon mounted on the distal extremity of the tubular member and disposed concentrically about the second tubular section with the second tubular section extending along substantially the entire length of balloon, the proximal end of the balloon joined to the distal end of the first tubular section and the distal end of the balloon joined to the second tubular section and with the second longitudinally extending lumen in the first tubular section in fluid communication with the interior of the inflatable balloon.

2. The dilatation catheter of claim 1 wherein a third tubular section is joined on the proximal end thereof to the distal end of the second tubular member and is formed of polymeric material more flexible than the polymeric material from which the second tubular member is made.

3. The catheter of claim 2 wherein the tubular sections are fabricated of polyethylene tubing of differing flexibilities, the junction between the second and third tubular sections are heat melted together, and the distal end of the balloon is joined by heat sealing to the third tubular section over the entire length thereof.

4. The catheter of claim 3 wherein the first and second tubular sections have a junction therebetween formed by heat melting.

5. The catheter of claim 2 wherein the tubular sections are fabricated of polyester tubing of differing flexibilities, the junction between the second and third tubular sections are heat melted together, and the distal end of the balloon is bonded adhesively to the third tubular section in a relatively narrow band near the proximal end thereof.

6. The catheter of claim 1 wherein the first and second tubular sections are fabricated of polyethylene tubing having differing flexibilities.

7. The catheter of claim 1 wherein the first and second tubular sections are fabricated of polyester tubing having differing flexibilities.

8. The catheter of claim 1 wherein the proximal end of the balloon is joined to the tubular member directly over the junctions between the first and second tubular sections to provide smooth transitions in flexibility along the length of the catheter.

9. In a dilatation catheter for use in transluminal angioplasty: a first shaft section fabricated of a relatively flexible material having first and second longitudinally extending luminal openings positioned side by side, a second shaft section fabricated of a material stiffer than the first shaft section having a single luminal opening heat melted to the distal end of the first shaft section with the first luminal opening extending through the junction and opening through the side wall of the second shaft section and the second luminal opening communicating with the single luminal opening in the second shaft section, a third shaft section fabricated of a material more flexible than the second shaft section having a single luminal opening heat melted to the distal end of the second shaft section with the luminal openings of the second and third shaft sections communicating with each other, and a distensible tubular balloon disposed about the second shaft section and closed at its proximal and distal ends by sealing to the shaft sections over the melted junctions between the shaft sections with the interior of the balloon communicating with the first luminal opening in the first shaft section through the opening in the wall of the second shaft section.

10. The catheter of claim 9 wherein the heat melted junction between the second and third shaft sections extends the entire length of the third shaft section.

11. The catheter of claim 10 wherein the shaft sections are fabricated of polyethylene tubing, and the distal end portion of the balloon is heat sealed to the shaft sections over the entire length of the third shaft section.

12. The catheter of claim 10 wherein the shaft sections are fabricated of polyester tubing, and the distal end portion of the balloon is adhesively bonded to the shaft sections in a relatively narrow band near the proximal end of the third shaft section.

13. In a method of manufacturing a dilatation catheter for use in transluminal angioplasty, the steps of: providing a first shaft section of relatively flexible material with first and second longitudinally extending luminal openings positioned side by side therein, joining a second shaft section of relatively stiff material with a single luminal opening to the distal end of the first shaft section with the first luminal opening extending through the junction and opening through the side wall of the second shaft section and the second luminal opening communicating with the single luminal opening in the second shaft section, joining a third shaft section of relatively flexible material with a single luminal opening to the distal end of the second shaft section with the luminal openings of the second and third shaft sections communicating with each other, positioning a distensible tubular member over the second shaft section, and bonding the end portions of the tubular member to the shaft sections over the junctions between the shaft sections to form an inflatable balloon which communicates with the first luminal opening in the first shaft section through the opening in the side wall of the second shaft section.

14. The method of claim 13 wherein the shaft sections are joined together by heat melting.

15. The method of claim 14 wherein the proximal and distal end portions of the tubular member are bonded to the shaft sections by heat sealing.

16. The method of claim 14 wherein the proximal end portion of the tubular member is bonded to the shaft sections by heat bonding, and the distal end portion of the tubular member is adhesively bonded to the shaft sections.

* * * * *